(12) United States Patent
Dunn

(10) Patent No.: US 8,187,640 B2
(45) Date of Patent: May 29, 2012

(54) LOW VISCOSITY LIQUID POLYMERIC DELIVERY SYSTEM

(75) Inventor: Richard L. Dunn, Fort Collins, CO (US)

(73) Assignee: Dunn Research & Consulting, LLC, Fort Collins, CO (US)

( * ) Notice: Subject to any disclaimer, the term of this patent is extended or adjusted under 35 U.S.C. 154(b) by 0 days.

(21) Appl. No.: 12/812,670

(22) PCT Filed: Jan. 13, 2009

(86) PCT No.: PCT/US2009/030853
§ 371 (c)(1),
(2), (4) Date: Oct. 19, 2010

(87) PCT Pub. No.: WO2009/091737
PCT Pub. Date: Jul. 23, 2009

(65) Prior Publication Data
US 2011/0027389 A1     Feb. 3, 2011

(51) Int. Cl.
*C08G 63/08* (2006.01)
*A61F 2/00* (2006.01)
*A61K 9/22* (2006.01)

(52) U.S. Cl. ........ 424/649; 424/426; 424/486; 528/354; 604/891.1

(58) Field of Classification Search .................. None
See application file for complete search history.

(56) References Cited

U.S. PATENT DOCUMENTS

| | | | |
|---|---|---|---|
| 3,297,033 A | 1/1967 | Schmitt et al. |
| 3,636,956 A | 1/1972 | Schneider |
| 3,773,919 A | 11/1973 | Boswell et al. |
| 3,887,699 A | 6/1975 | Yolles |
| 4,155,992 A | 5/1979 | Schmitt |
| 4,186,189 A | 1/1980 | Shalaby et al. |
| 4,379,138 A | 4/1983 | Pitt et al. |
| 4,523,591 A | 6/1985 | Kaplan et al. |
| 4,530,840 A | 7/1985 | Tice et al. |
| 4,582,052 A | 4/1986 | Dunn et al. |
| 4,650,488 A | 3/1987 | Bays et al. |
| 4,655,777 A | 4/1987 | Dunn et al. |
| 4,767,628 A | 8/1988 | Hutchinson |
| 4,804,691 A | 2/1989 | English et al. |
| 4,808,691 A | 2/1989 | König et al. |
| 4,841,968 A | 6/1989 | Dunn et al. |
| 4,891,225 A | 1/1990 | Langer et al. |
| 4,906,474 A | 3/1990 | Langer et al. |
| 4,938,763 A | 7/1990 | Dunn et al. |
| 4,950,735 A | 8/1990 | Vanderbilt et al. |
| 4,975,271 A | 12/1990 | Dunn et al. |
| 5,068,220 A | 11/1991 | Vanderbilt et al. |
| 5,077,049 A | 12/1991 | Dunn et al. |
| 5,160,737 A | 11/1992 | Friedman et al. |
| 5,242,910 A | 9/1993 | Damanj |
| 5,278,201 A | 1/1994 | Dunn et al. |
| 5,278,202 A | 1/1994 | Dunn et al. |
| 5,324,519 A | 6/1994 | Dunn et al. |
| 5,324,520 A | 6/1994 | Dunn et al. |
| 5,340,849 A | 8/1994 | Dunn et al. |
| 5,368,859 A | 11/1994 | Dunn et al. |
| 5,442,033 A | 8/1995 | Bezwada |
| 5,464,929 A | 11/1995 | Bezwada et al. |
| 5,466,444 A | 11/1995 | Jurgens |
| 5,487,897 A | 1/1996 | Polson et al. |
| 5,576,418 A | 11/1996 | Jurgens |
| 5,599,552 A | 2/1997 | Dunn et al. |
| 5,599,852 A | 2/1997 | Scopelianos et al. |
| 5,620,700 A | 4/1997 | Berggren et al. |
| 5,631,015 A | 5/1997 | Bezwada et al. |
| 5,632,727 A | 5/1997 | Tipton et al. |
| 5,653,992 A | 8/1997 | Bezwada et al. |
| 5,660,849 A | 8/1997 | Polson et al. |
| 5,702,716 A | 12/1997 | Dunn et al. |
| 5,707,647 A | 1/1998 | Dunn et al. |
| 5,717,030 A | 2/1998 | Dunn et al. |
| 5,722,950 A | 3/1998 | Fujita et al. |
| 5,725,491 A | 3/1998 | Tipton et al. |
| 5,728,752 A | 3/1998 | Scopelianos et al. |
| 5,733,950 A | 3/1998 | Dunn et al. |
| 5,736,152 A | 4/1998 | Dunn |
| 5,739,176 A | 4/1998 | Dunn et al. |
| 5,744,153 A | 4/1998 | Yewey et al. |
| 5,747,058 A | 5/1998 | Tipton et al. |
| 5,747,637 A | 5/1998 | Shinoda et al. |
| 5,759,563 A | 6/1998 | Yewey et al. |
| 5,780,044 A | 7/1998 | Yewey et al. |
| 5,783,205 A | 7/1998 | Berggren et al. |
| 5,792,469 A | 8/1998 | Tipton et al. |
| 5,824,333 A | 10/1998 | Scopelianos et al. |

(Continued)

FOREIGN PATENT DOCUMENTS

EP     0 499 164 A1    8/1992

(Continued)

OTHER PUBLICATIONS

Padula, "GnRH analogues—agonists and antagonists", Animal Reproduction Science, 2005, vol. 88, issues 1-2, pp. 115-126.*

(Continued)

*Primary Examiner* — Jeffrey S. Lundgren
*Assistant Examiner* — Stephanie Springer
(74) *Attorney, Agent, or Firm* — Whyte Hirschboeck Dudek S.C.

(57) ABSTRACT

Low viscosity biodegradable polymer solutions of a liquid biodegradable polymer and biocompatible solvent and methods of using the compositions to form a biodegradable liquid polymer implant are provided.

30 Claims, No Drawings

U.S. PATENT DOCUMENTS

| | | | |
|---|---|---|---|
| 5,888,533 | A | 3/1999 | Dunn |
| 5,945,115 | A | 8/1999 | Dunn et al. |
| 5,962,006 | A | 10/1999 | Southard et al. |
| 5,968,542 | A | 10/1999 | Tipton |
| 5,990,194 | A | 11/1999 | Dunn et al. |
| 6,051,558 | A | 4/2000 | Burns et al. |
| 6,071,530 | A | 6/2000 | Polson et al. |
| 6,120,789 | A | 9/2000 | Dunn |
| 6,130,200 | A | 10/2000 | Brodbeck et al. |
| 6,143,314 | A | 11/2000 | Chandrashekar et al. |
| 6,177,094 | B1 | 1/2001 | Jiang |
| 6,238,705 | B1 | 5/2001 | Liu et al. |
| 6,245,345 | B1 | 6/2001 | Swanbom et al. |
| 6,261,583 | B1 | 7/2001 | Dunn et al. |
| 6,291,013 | B1 | 9/2001 | Gibson et al. |
| 6,331,311 | B1 | 12/2001 | Brodbeck et al. |
| 6,335,383 | B1 | 1/2002 | Scopelianos et al. |
| 6,352,667 | B1 | 3/2002 | English |
| 6,395,293 | B2 | 5/2002 | Polson et al. |
| 6,413,536 | B1 | 7/2002 | Gibson et al. |
| 6,458,385 | B2 | 10/2002 | Jamiolkowski et al. |
| 6,461,631 | B1 | 10/2002 | Dunn et al. |
| 6,468,961 | B1 | 10/2002 | Brodbeck et al. |
| 6,482,872 | B2 | 11/2002 | Downie |
| RE37,950 | E | 12/2002 | Dunn et al. |
| 6,528,080 | B2 | 3/2003 | Dunn et al. |
| 6,537,565 | B2 | 3/2003 | Swanbom et al. |
| 6,565,874 | B1 | 5/2003 | Dunn et al. |
| 6,585,994 | B2 | 7/2003 | Williams et al. |
| 6,613,355 | B2 | 9/2003 | Ng et al. |
| 6,630,155 | B1 | 10/2003 | Chandrashekar et al. |
| 6,673,767 | B1 | 1/2004 | Brodbeck et al. |
| 6,685,697 | B1 | 2/2004 | Arenberg et al. |
| 6,726,920 | B1 | 4/2004 | Theeuwes et al. |
| 6,730,772 | B2 | 5/2004 | Shastri |
| 6,733,767 | B2 | 5/2004 | Chern et al. |
| 6,773,714 | B2 | 8/2004 | Dunn et al. |
| 6,790,458 | B2 | 9/2004 | Ng et al. |
| 6,818,018 | B1 | 11/2004 | Sawhney |
| 6,835,194 | B2 | 12/2004 | Johnson et al. |
| 6,861,068 | B2 | 3/2005 | Ng et al. |
| 6,872,799 | B2 | 3/2005 | Nathan |
| 6,916,788 | B2 | 7/2005 | Seo et al. |
| 6,967,234 | B2 | 11/2005 | Nathan |
| 6,992,065 | B2 | 1/2006 | Okumu |
| 7,005,136 | B2 | 2/2006 | Nathan et al. |
| 7,053,209 | B1 | 5/2006 | Gibson et al. |
| 7,128,927 | B1 | 10/2006 | Dunn |
| 7,288,542 | B2 | 10/2007 | Dunn et al. |
| 7,326,426 | B2 | 2/2008 | Nathan et al. |
| 7,666,891 | B2 | 2/2010 | Dunn et al. |
| 7,785,628 | B2 | 8/2010 | Hissink et al. |
| 2001/0033853 | A1 | 10/2001 | Swanbom et al. |
| 2002/0001608 | A1 | 1/2002 | Polson et al. |
| 2002/0034532 | A1 | 3/2002 | Brodbeck et al. |
| 2002/0090398 | A1 | 7/2002 | Dunn et al. |
| 2003/0044467 | A1 | 3/2003 | Brodbeck et al. |
| 2003/0104031 | A1 | 6/2003 | Dumont et al. |
| 2003/0133964 | A1 | 7/2003 | Dunn et al. |
| 2003/0147934 | A1* | 8/2003 | Hissink et al. ............ 424/423 |
| 2003/0157178 | A1 | 8/2003 | Chen et al. |
| 2003/0170289 | A1 | 9/2003 | Chen et al. |
| 2003/0180364 | A1 | 9/2003 | Chen et al. |
| 2003/0185752 | A1 | 10/2003 | Nathan et al. |
| 2003/0211974 | A1 | 11/2003 | Brodbeck et al. |
| 2004/0022859 | A1 | 2/2004 | Chen et al. |
| 2004/0024069 | A1 | 2/2004 | Chen et al. |
| 2004/0101557 | A1 | 5/2004 | Gibson et al. |
| 2004/0127846 | A1 | 7/2004 | Dunn et al. |
| 2004/0146557 | A1 | 7/2004 | Chern et al. |
| 2004/0229912 | A1 | 11/2004 | Dunn et al. |
| 2005/0215554 | A1 | 9/2005 | Dunn et al. |
| 2006/0013879 | A9 | 1/2006 | Brodbeck et al. |
| 2006/0025462 | A1 | 2/2006 | Dunn et al. |
| 2006/0121085 | A1 | 6/2006 | Warren et al. |
| 2006/0210599 | A1 | 9/2006 | Gibson et al. |
| 2006/0210604 | A1 | 9/2006 | Dadey et al. |
| 2007/0104759 | A1 | 5/2007 | Dunn et al. |
| 2007/0161097 | A1 | 7/2007 | Green et al. |
| 2007/0184084 | A1 | 8/2007 | Chen et al. |
| 2009/0124535 | A1 | 5/2009 | Markland et al. |
| 2009/0181068 | A1 | 7/2009 | Dunn |

FOREIGN PATENT DOCUMENTS

| | | |
|---|---|---|
| EP | 0 635 531 A2 | 1/1995 |
| WO | 96/21427 A1 | 7/1996 |
| WO | 99/47073 A1 | 9/1999 |
| WO | WO 2006053175 A2 * | 5/2006 |

OTHER PUBLICATIONS

International Application No. PCT/US2009/030853 Notification of Transmittal of The International Preliminary Report on Patentability; dated Jun. 8, 2010; 9 pages.

International Application No. PCT/US2009/030853 (Publ. No. WO 2009/091737A3) International Search Report; dated Jan. 4, 2010; 4 pages.

Al-Tahami et al., "Smart Polymer Based Delivery Systems for Peptides and Proteins", Recent Patents on Drug Delivery & Formulation, vol. 1, No. 1, 2007 (pp. 65-71).

ATRISORB® FreeFlow™, "Bioabsorbable Guided Tissue Regeneration (GTR) Barrier," Instructions for Use, Rev. 6, Dec. 2008 (2 pgs.).

ATRIX Laboratories, "Material Safety Data Sheet," available at http://www.atridox.com/dental/Atridox_MSDS.pdf, Oct. 14, 1997 (7 pgs.).

CollaGenex, ATRIDOX® (doxycycline hyclate) 10%, "Antimicrobial action right where you want it™," Jun. 2002 (2 pgs.).

CollaGenex, ATRISORB® FreeFlow™, available at http://www.collagenex.com/pr_atrisorb.asp, available at least by Jul. 6, 2004 (2 pgs.).

CollaGenex, ATRISORB® Product Info, For Dental professionals, available at http://www.atrisorb.com/Dental/dental2.html, Dec. 25, 2007 (2 pgs.).

DesNoyer et al., "Role of crystallization in the phase inversion dynamics and protein release kinetics of injectable drug delivery systems," Journal of Controlled Release, vol. 70, 2001 (pp. 285-294).

DesNoyer et al., "The effect of Pluronic on the protein release kinetics of an injectable drug delivery system", Journal of Controlled Release, vol. 86, 2003 (pp. 15-24).

DURECT: Patents, available at http://www.durect.com/wt/durect/page_name/patents, Oct. 25, 2007 (4 pgs.).

DURECT: SABER System™, available at http://www.durect.com/wt/durect/page_name/saber, Oct. 17, 2007 (1 pg.).

Eliaz et al., "Injectable System for In-Situ Forming Solid Biodegradable Protein Delivery", Proceed. Intern. Symp. Control. Rel. Bioact. Mater., vol. 23, 1996 (pp. 841-842).

Hatefi et al., "Biodegradable injectable in situ forming drug delivery systems", Journal of Controlled Release, vol. 80, 2002 (pp. 9-28).

LACTIDE, "Biodegradable and Biorenewable Materials Based on Lactic Acid", available at http://www.cem.msu.edu/~smithmr/Lactide.htm, Oct. 5, 2010 (3 pgs.).

Lambert et al., "Development of an in situ forming biodegradable poly-lactide-co-glycolide system for the controlled release of proteins", Journal of Controlled Release, vol. 33, 1995 (pp. 189-195).

Matschke et al., "Sustained-release injectables formed in situ and their potential use for veterinary products", Journal of Controlled Release, vol. 85, 2002 (pp. 1-15).

Packhaeuser et al., "In situ forming parenteral drug delivery systems: an overview", European Journal of Pharmaceutics and Biopharmaceutics, vol. 58, 2004 (pp. 445-455).

QLT Inc.—Development—ATRIGEL® Drug Delivery, available at http://www.qltinc.com/Qltinc/main/mainpages.cfm?InternetPageID=232, last modified on Jul. 13, 2006 (2 pgs.).

QLT Inc.—Development—ELIGARD®, available at http://www.qltinc.com/Qltinc/main/mainpages.cfm?InternetPageID=227, last modified on Mar. 1, 2006 (1 pg.).

QLT Inc.—Drug Delivery Platform, Atrigel, available at http://www.qltinc.com/Qltinc/_downloads/development/development_atrigel_sheet_2006.pdf, 2006 (2 pgs.).

Raman et al., "A model for drug release from fast phase inverting injectable solutions", Journal of Controlled Release, vol. 102, 2005 (pp. 145-157).

Shah et al., "A biodegradable injectable implant for delivering micro and macromolecules using poly (lactic-co-glycolic) acid (PLGA) copolymers", Journal of Controlled Release, vol. 27, 1993 (pp. 139-147).

Shim et al., "Poly(D,L-lactic acid-co-glycolic acid)-b-poly(ethylene glycol)-b-poly(D,L-lactic acid-co-glycolic acid) triblock copolymer and thermoreversible phase transition in water", Journal of Biomedical Materials Research, vol. 61, Issue 2, Aug. 2002 (pp. 188-196).

Tipton et al., "In Situ Gelling Systems", Sustained-Release Injectable Products, ed., Interpharm Press, 2000 (pp. 241-278).

Wang et al., "Structure formation in injectable poly(lactide-co-glycolide) depots", Journal of Controlled Release, vol. 90, 2003 (pp. 345-354).

* cited by examiner

LOW VISCOSITY LIQUID POLYMERIC DELIVERY SYSTEM

FIELD OF THE INVENTION

Embodiments of the present invention relate to methods and compositions for producing low viscosity biodegradable polymer solutions comprising liquid biodegradable polymers and biocompatible solvent that can be easily administered to the body where the biocompatible solvent dissipates in body fluid leaving a liquid polymer implant. The biodegradable liquid polymer implants are suitable for the delivery of biologically active agents and for use as medical or surgical devices.

BACKGROUND OF THE INVENTION

Biodegradable polymers are well known for their use in biomedical applications such as sutures, surgical clips, staples, implants, and drug delivery systems. These polymers include the polyglycolides, polylactides, polycaprolactones, polyanhydrides, polyorthoesters, polydioxanones, polyacetals, polyesteramides, polyamides, polyurethanes, polycarbonates, poly(amino acids), polyphosphazenes, polyketals, polyhydroxybutyrates, polyhydroxyalerates, and polyalkylene oxalates. Examples of their uses are described in U.S. Pat. No. 3,297,033 to Schmitt, U.S. Pat. No. 3,636,956 to Schneider, U.S. Pat. No. 4,523,591 to Kaplan, U.S. Pat. No. 3,773,919 to Boswell, U.S. Pat. No. 3,887,699 to Yolles, U.S. Pat. No. 4,155,992 to Schmitt, U.S. Pat. No. 4,379,138 to Pitt et al., U.S. Pat. No. 4,186,189 to Shalaby et al., U.S. Pat. No. 4,767,628 to Hutchinson, U.S. Pat. No. 4,530,840 to Tice, et al., and U.S. Pat. No. 4,891,225 and U.S. Pat. No. 4,906,474 to Langer.

All of the biodegradable polymers described in the foregoing patents are solid materials used to form solid articles such as sutures, staples, surgical clips, implants or microcapsules and microparticles. Because these polymers are solids, all of their applications in the biomedical field require that the polymeric structures be formed outside the body, and then inserted into the body for their use. Sutures, clips, and staples are normally placed in the body during a surgical procedure. Solid implants for drug delivery are either surgically placed or inserted into the body using large diameter trochars. Only the microparticles including microcapsules and microspheres can be injected using standard syringes and needles. However, the manufacture of microparticles and nanoparticles is a difficult process with many variables that have to be controlled to obtain reproducible drug delivery systems. These include solvent selection, polymer and drug concentration, temperature, stirring speed, drug loading, particle size, coating uniformity, and porosity. Because the drug is in contact with the polymer during the manufacturing steps and on storage, sterility and stability issues are normally encountered. In addition, a great deal of the drug is lost if the encapsulation efficiency is not high during the manufacturing process.

Dunn et al., in U.S. Pat. Nos. 4,938,763 and 5,278,201 have overcome the administration problems with the solid implants by dissolving the solid biodegradable polymers in a biocompatible solvent and injecting the solution into the body using standard syringes and needles where the polymer in the solution precipitates or coagulates upon contact with aqueous body fluid to form a solid implant matrix. The delivery system described in these patents offer a number of advantages including the ease of manufacture of the polymer solution, the incorporation of the drug into the polymer solution just prior to administration leading to increased drug and polymer stability as well as no loss of drug during the manufacturing process, and the ability to terminally sterilize the polymer solution as well as the drug. However, there are some disadvantages with this in-situ forming polymer system. Because the polymers used are solids with relative high molecular weights, the polymer solutions formed from the combination of the solid polymers and the biocompatible solvents are quite viscous. With the high solution viscosities, 18-21 gauge needles are required for administration and considerable injection force is needed. In addition, the viscous solutions are not easily injected into muscle tissue and the solid implants formed from these polymer solutions tend to cause local irritation of the muscular tissue. For this reason, the foregoing polymer solutions are normally injected subcutaneously where the material forms quite distinct and noticeable bumps.

Bezwada et al. in U.S. Pat. No. 5,442,033 have attempted to overcome the use of solvents in the Dunn delivery system and the formation of solid implant bumps by using liquid biodegradable polymers of caprolactone and lactide. In later patents including U.S. Pat. No. 5,631,015; U.S. Pat. No. 5,653,992; U.S. Pat. No. 5,599,852; U.S. Pat. No. 5,728,752; and U.S. Pat. No. 6,335,383, both Bezwada and Scopelianos et al. have extended this concept by using a variety of caprolactone, trimethylene carbonate, and ether lactone copolymers or terpolymers with glycolide, lactide, or p-dioxanone to form liquid biodegradable polymers which are injected into the body without the use of solvents to form liquid implants used as medical devices. Both Bezwada and Scopelianos indicate that the use of solvents with the Dunn delivery system is a major disadvantage which they have overcome with their liquid polymers. However, these liquid polymers are very viscous materials with viscosities normally much greater than 5,000 cP at 37° C., and they require large 16-18 gauge needles with special syringes and a high injection force for administration into the body. The high viscosities of the liquid polymers and the need for special syringes and large needles are major disadvantages of the Bezwada and Scopelianos systems.

Tipton et al. in U.S. Pat. No. 5,747,058 and Gibson et al. in U.S. Pat. No. 7,053,209 have found that highly viscous, non-polymeric, non-water soluble liquid materials with viscosities of at least 5,000 cP at 37° C., can also be used as liquid implants for drug delivery. They further describe the use of biocompatible solvents to reduce the viscosity of the high viscosity nonpolymeric liquids to levels less than 1,000 cP so as to enable administration of the material into the body with smaller gauge needles. All of these materials are nonpolymeric and would be expected to show low viscosities when dissolved in a biocompatible solvent. Even solid nonpolymeric materials as described by Dunn et al. in U.S. Pat. No. 5,736,152, when dissolved in biocompatible solvents, form non-viscous solutions which can be injected into the body with standard syringes and needles to form nonpolymeric implants having a solid matrix that has a firm consistency ranging from gelatinous to impressionable and moldable, to a hard, dense solid. However, the problem with nonpolymeric materials is that their degradation times in the body cannot be varied, as they are nonpolymeric with only one molecular weight. In addition, their release characteristics cannot be modified by changing the molecular composition as can be achieved with polymeric materials.

Therefore, there exists a need for a method and composition for providing liquid polymeric implants with low viscosities for easy administration into the body using standard syringes and needles.

There also exists a further need for a method and composition for providing more syringeable liquid implants which are biodegradable and can be used as medical or surgical devices and/or controlled delivery systems.

In addition, there is the need for such liquid implants in which the polymer biodegradation and drug release characteristics can be varied over a wide range of time and rates.

SUMMARY OF THE INVENTION

The present invention relates to compositions composed of liquid biodegradable polymers combined with biocompatible organic solvents and the use of the polymer compositions, for example, as drug delivery systems or medical or surgical devices. In embodiments of the invention, liquid biodegradable polymers are dissolved in nontoxic biocompatible organic solvents to form low viscosity solutions that can be easily injected into the body with standard syringes and small gauge needles. Once the liquid polymer solution is placed within the body, the solvent dissipates or diffuses away from the polymer leaving a more viscous liquid polymer implant suitable, for example, for delivery of a biologically active agent or for use as a medical or surgical device. Because the polymer composition is a low viscosity liquid, it can be injected into muscle or subcutaneous tissue without damage to the surrounding tissue and without the noticeable bump observed with solid implants.

In some embodiments, the liquid polymer/solvent composition can be used to form a medical or surgical implant by injection directly into a tissue site where the material will form a polymer film or coating, plug or other structure that remains in a liquid form or consistency after the solvent has dissipated. The liquid polymer in the form of a film can be used, for example, to separate tissues to prevent the formation of surgical adhesions. The liquid polymer/solvent composition can also be used to coat or cover an in-dwelling catheter or other device. The liquid polymer/solvent composition can also be applied to form a plug or other liquid mass that can be used, for example, to temporarily seal tissue tears or holes.

In other embodiments, the liquid polymer/solvent composition can be used as a system for delivery of a biologically active agent (e.g., drug), which can be dissolved or dispersed into the liquid polymer/biocompatible solvent solution. When the liquid polymer/solvent composition with the dissolved or dispersed active agent is injected into the body, the organic solvent upon exposure to an aqueous medium (e.g., body fluids) will dissolve or diffuse away from the liquid polymer component leaving a viscous liquid polymer implant with the active agent entrapped or encapsulated therein. The hydrophilic or hydrophobic characteristic of the liquid polymer combined with its rate of degradation within the body can be used to control the release of the active agent over a desired time period.

An embodiment of a method according to the invention includes administering to a subject (e.g., patient) in need of a treatment or prevention, for example, an effective amount of the liquid polymer/solvent composition of the present invention, optionally with a bioactive agent. Another embodiment of a method of the invention includes applying the liquid polymer/solvent composition, optionally with a bioactive agent, to a device such as a catheter, and inserting the coated device into the body of a subject for a desired treatment or procedure.

The present liquid polymer/solvent compositions provide the advantages of liquid application to form medical or surgical devices and/or delivery systems for active agents (e.g., drugs). The present liquid polymer/solvent compositions also allow the use of smaller gauge needles compared to other liquid polymer systems made without a solvent. The solvents used in the present compositions allow an active agent to also be administered as a solution in contrast to liquid polymer systems made without solvents. The use of liquid biodegradable polymers in the present system also allows the rate of release of an active agent and degradation of the liquid implant to be varied over a wide range in contrast to the nonpolymeric liquid implant systems.

DETAILED DESCRIPTION OF THE INVENTION

The compositions of the present invention relate to solutions of a biodegradable liquid polymer(s) combined with a biocompatible organic solvent(s) that dissolves or dissipates when the liquid polymer/solvent compositions are placed in a body to form a viscous liquid polymer material in the form of a film, a coating, a plug or other mass. The implanted polymer compositions can be used, for example, as a medical or surgical device and/or a delivery system for a biologically active agent (e.g., drug).

As used herein, the term "liquid" refers to the ability of the composition and/or the liquid polymer materials or implants to undergo continuous deformation under a shearing stress. Liquid polymer compositions according to the invention possess a viscosity, density and flowability to allow delivery of the composition through small gauge needles (e.g., 18-26 gauge) with low to moderate injection force using standard syringes. The liquid polymer materials and implants have a definite volume, but are an amorphous liquid mass with no definite shape. The term "polymer" refers generally to polymers, copolymers and/or terpolymers that can be linear, branched, grafted and/or star-shaped.

Solid polymers have been extensively used in extended release systems such as implants, microparticles, and gels because the solid polymer provides a barrier to diffusion or dissolution of the drug from the polymer matrix. By comparison, liquid polymers with their amorphous structure typically do not provide an extended release of a drug and therefore have seldom been used in drug release systems. Organic solvents have been used in drug delivery to dissolve a drug so that it could be administered to the body, but the solvents, themselves, do not provide an extended release of a drug. As a result, conventional belief has been that the use of liquid polymers combined with biocompatible organic solvents to form liquid polymer implants would release a drug or other active agent much too fast to provide any sustained activity because of the rapid diffusion of the active agent through a liquid matrix rather than a solid matrix when placed into the body. In addition, the rapid release from the liquid polymer/solvent system would be expected to lead to an unacceptable initial burst of the drug from the implant. Contrary to this belief, it was surprisingly found that the present liquid polymer/solvent solutions form implants that do not solidify and remain as a viscous liquid form upon injection into the body while providing comparable initial burst and extended release of drugs and other active agents as those observed with implants formed from solid polymer/solvent solutions. The present combination of liquid biodegradable polymers with biocompatible solvents provides readily injectable and sterile filterable formulations. The liquid implant material is biocompatible and the formulations can be injected into body tissue without tissue irritation and noticeable bumps associated with solid implants.

The compositions are prepared by mixing or blending together the liquid polymer(s) and the organic solvent(s), which can be performed by any method at a temperature ranging from about 10-50° C. (e.g., at about 25° C.) using a suitable device to achieve a homogeneous, flowable liquid at room temperature. Examples of such devices include a mechanical stirrer, a mixer, or a roller mill. Because both the polymer and solvents are liquids, they are readily mixed to form a homogeneous solution.

The liquid polymers that can be used according to the present invention are biodegradable and/or bioabsorbable, remain in a liquid (flowable) form at room temperature (i.e., at 25° C.) up to body temperature (i.e., at 37° C.), and have a bulk viscosity that allows the composition to be easily administered, and in some embodiments effective to provide a desired controlled release profile of a biologically active agent from the implanted material. Because the liquid polymer materials are already liquids at room temperature, they allow the use of lower concentrations of the biocompatible solvent to be used in the composition to provide a syringeable formulation compared to polymer/solvent compositions prepared with solid polymers.

Examples of suitable polymers which can be used in this application include polylactic acid, polyglycolic acid, polylactide (dl-lactide, d-lactide, l-lactide), polyglycolide, polycaprolactones, polyanhydrides, polyamides, polyurethanes, polyesteramides, polyorthoesters, polydioxanones, polyacetals, polyketals, polycarbonates, polyphosphazenes, polyhydroxybutyrates, polyhydroxyvalerates, polyalkylene oxalates, polyalkylene succinates, poly(malic acid), polyethylene glycol, hyaluronic acid, chitin and chitosan, and copolymers, terpolymers, and combinations or mixtures of the above materials. Preferred materials include those polymers, copolymer or terpolymers made with lactide, glycolide, caprolactone, p-dioxanone, trimethylene carbonate, 1,5-dioxepan-2-one, 1,4-dioxepan-2-one, ethylene oxide, propylene oxide, sebacic anhydride, diketene acetals/diols, and lactic acid with lower molecular weights and amorphous regions to limit crystallinity and subsequent solidification. Non-limiting examples of suitable liquid polymers according to the invention include copolymers of L-lactide and ε-caprolactone with molar ratios of lactide/caprolactone ranging from about 65/35 to about 50/50 with inherent viscosities as determined in a 0.10 g/dL solution of hexafluoroisopropanol (HFIP) at 25° C. from about 0.06 to about 0.38 dL/g, copolymers of caprolactone and 1,4-dioxanone with molar ratios of about 70/30 to about 40/60 and inherent viscosities of about 0.08 to about 0.24 dL/g, copolymers of caprolactone and trimethylene carbonate with molar ratios of about 90/10 to about 50/50 with inherent viscosities of about 0.09 to about 0.25 dL/g, and poly(L-lactic acid) with an inherent viscosity of about 0.06 dL/g, among others. By comparison, copolymers of L-lactide and caprolactone with a molar ratio of 90/10 and inherent viscosities of 0.24 to 0.30 dL/g and copolymers of caprolactone and 1,4-dioxanone with molar ratios of 90/10 to 80/20 and inherent viscosities of 0.23 to 0.32 dL/g are solids at room temperature. In embodiments of the composition, the biodegradable liquid polymer is a copolymer of lactide and caprolactone having a molar ratio of about 75/25 to about 25/75 with a preferred ratio of about 50/50, and a molecular weight of about 2,000 daltons to about 20,000 daltons with a preferred molecular weight of about 3,000 to about 12,000 daltons, as determined by gel permeation chromatography using a multi-angle light-scattering detector (GPC-MALS).

Solvents that can be used according to the invention are non-toxic and can be either hydrophilic or lipophilic depending upon the desired release profile and the solubility of the polymer and/or biologically active agent in the polymer/solvent composition. A hydrophilic organic solvent will quickly dissolve in body fluids leaving the liquid polymer material as an implant, for example, in the form of a film, coating or plug. If a drug or other active agent is dissolved in a liquid polymer/hydrophilic solvent composition, the active agent will become encapsulated or entrapped in the liquid polymer material as the hydrophilic solvent dissolves or dissipates into the body fluid. If a lipophilic solvent is used, the dissolution or diffusion of the lipophilic solvent into surrounding aqueous tissue fluid will be relatively slow with a resultant slower increase in viscosity of the administered polymer/solvent composition. However, a lipophilic solvent, by its own nature, will slow the release of a biological active agent incorporated into the composition until the solvent has dissipated, leaving the liquid polymer implant with the entrapped active agent. By adjusting the hydrophilicity/lipophilicity character of the polymer and/or the solvent, the release of the biologically active agent can be controlled to provide a low initial burst and sustained release of both hydrophilic and lipophilic drugs (or other active agent). In addition, the solubility of a hydrophilic or lipophilic biologically active agent can be controlled to provide either solutions or dispersions of the active agent in the liquid polymer/solvent compositions.

Suitable hydrophilic biocompatible organic solvents that can be used according to the present invention have a water solubility greater than 10% by weight of the solvent in water. Examples of hydrophilic biocompatible organic solvents include amides such as N-methyl-2-pyrrolidone (NMP), 2-pyrrolidone, N-ethyl-2-pyrrolidone, N-cyclohexyl-2-pyrrolidone, N-hydroxyethyl-2-pyrrolidone, dimethyl acetamide, and dimethyl formamide; acids such as acetic acid and lactic acid; alcohols such as ethanol and propanol; esters of monobasic acids such as methyl lactate, ethyl lactate, and methyl acetate; ether alcohols such as diethylene glycol monomethyl ether, glycofurol, glycerol formal, and isopropylidene glycerol (Solketal); sulfoxides such as dimethyl sulfoxide; lactones such as e-caprolactone and butyrolactone; polyhydroxy alcohols such as propylene glycol, polyethylene glycol, glycerol, and 1,3-butyleneglycol; esters of polyhydroxy alcohols such as methoxypolyethylene glycol and methoxypropylene glycol; ketones such as acetone and methyl ethyl ketone; and ethers such as tetrahydrofuran. Preferred hydrophilic solvents include N-methyl-2-pyrrolidone, 2-pyrrolidone, dimethyl acetamide, dimethyl sulfoxide, ethyl lactate, glycofurol, glycerol formal, isopropylidene glycerol, propylene glycol, polyethylene glycol, methoxypolyethylene glycol and methoxypropylene glycol due to their solvating ability and tissue compatibility.

Suitable lipophilic biocompatible organic solvents that can be used according to the invention have a water solubility less than 10% by weight of the solvent in water. Examples of lipophilic biocompatible organic solvents include esters of mono-, di-, and tricarboxylic acids such as ethyl acetate, ethyl butyrate, ethyl oleate, isopropyl palmitate, ethyl palmitate, methyl palmitate, isopropyl myristate, diethyl malonate, diethyl succinate, dimethyl adipate, dimethyl succinate, dibutyl sebacate, triacetin, triethyl citrate, tributyrin, acetyl triethyl citrate, acetyl tributyl citrate, acetyl trihexyl citrate, butyryl trihexyl citrate, and tributyl citrate; esters of caprylic and/or capric acids with glycerol or alkylene glycols such as MIGLYOL 810 or 812 (caprylic/capric triglycerides), MIGLYOL 818 (caprylic/capric/linoleic triglyceride), MIGLYOL 829 (caprylic/capric/succinic triglyceride), and MIGLYOL 840 (propylene glycol dicaprylate/caprate); aromatic alcohols such as benzyl alcohol; esters of aromatic acids such as ethyl benzoate and benzyl benzoate; esters of carbonic acid such as propylene carbonate and dimethyl carbonate; amides such as N,N-diethyl-toluamide, N-dodecyl-2-pyrrolidone, N-octyl-2-pyrrolidone, N-methyl-2-caprolactam, and N-dodecyl-caprolactam; fatty acids such as heptanoic acid and oleic acid; and oils such as sesame oil, peanut oil, and castor oil. Preferred lipophilic solvents include ethyl acetate, ethyl oleate, isopropyl myristate, triacetin, triethyl citrate, acetyl tributyl citrate, ethyl benzoate, benzyl benzoate, and sesame oil.

Combinations of different hydrophilic solvents can be used to obtain higher or lower levels of solubility of the liquid polymer and bioactive agent in the resultant solution. A combination of organic solvents can also be used to control the rate of release of an active agent by controlling the rate at which the solvent dissolves or dissipates when the liquid polymer/solvent/active agent composition is placed in the body. Similarly, combinations of different lipophilic solvents can also be used to control the solubility of the liquid polymer and active agent in the solvent and the release of the active agent in the body. In other embodiments, combinations of hydrophilic and lipophilic solvents can be used to obtain the optimum solvent characteristics for a delivery system. Examples include a combination of N-methylpyrrolidone and triacetin which provides a more hydrophobic solvent than N-methylpyrrolidone alone, and a combination of N-methylpyrrolidone and ethanol which provides a more hydrophilic solvent than N-methylpyrrolidone alone.

The organic solvent is typically added to the compositions in an amount ranging from about 10 percent to about 70 percent by weight, relative to the total weight of the composition. Preferably, the solvent is present in the composition in an amount ranging from about 30 percent to about 60 percent by weight. The concentration of solvent allows for the level of liquid polymer in the composition to range from about 30 percent to about 90 percent by weight, preferably from about 40 percent to about 70 percent by weight relative to the overall composition. The liquid polymer/solvent concentrations permit the liquid polymer/solvent compositions to be easily injected with standard syringes and small gauge needles (e.g., about 18-26 gauge) unlike liquid polymer formulations previously described, for example, by Bezwada and Scopelianos, which in some embodiments, unlike the present compositions, require the addition of a particulate material to achieve an acceptable viscosity for injection with a syringe and needle. The compositions of the invention can be administered into the body of a human subject or animal such as a dog, cat, horse, etc.

The composition can be applied or injected into the body of a subject or onto an object (e.g., mesh, catheter, a screw, plate, tack, pin, staple, sponge, etc.) using a device such as a syringe or needle. A device with the composition thereon can be placed into the body of the subject. The liquid polymer component of the implanted polymer/solvent compositions of the invention will flow and fill the voids left by the organic solvent as it dissipates from the implanted material. The implanted liquid polymer material remains as a liquid or fluid (flowable) consistency but not a gelatinous or solid consistency nor a microporous solid or gelatinous matrix. The liquid polymer implant gradually biodegrades in the subject's body over time.

The liquid polymer/solvent compositions can be used, for example, for a variety of medical and surgical applications. For example, the liquid polymer/solvent compositions can be injected into or applied to soft tissue or surgical meshes to form a protective coating or film to prevent or minimize the formation of tissue adhesions. The compositions can also be applied as films, for example, to coat vascular grafts to prevent the formation of blood clots, as liquid plugs, for example, to seal fluid or air leaks, or as an injected material, for example, to repair or augment a body tissue. Because of the low solution viscosity, the liquid polymer/solvent compositions can be injected, for example, into facial tissues using small gauge needles (e.g. 18-26) to camouflage scars, fill depressions, and smooth out irregularities. The compositions can also be applied to restore or improve sphincter function, and as general purpose fillers in the body.

In other embodiments, the liquid polymer/solvent compositions can be used as controlled release implants to provide a delivery system in which a drug or other biologically active agent is added to the liquid polymer/solvent composition prior to injection in the body. Upon exposure to body fluid, the organic solvent dissolves or dissipates in the aqueous tissue fluid to leave the more viscous liquid polymer for release of the encapsulated or entrapped active agent. Surprisingly based upon the use of only solid polymers to form solid implants by Dunn et al. and the use of liquid polymers without any solvents described by Bezwada and Scopelianos, the liquid polymer implant formed from compositions of the present invention by the dissolution or dissipation of the solvent can be used to control the release of biologically active agents with low initial burst and extended release of the drug.

The rate of release of the active agent (e.g., drug) can be controlled by the composition of the biodegradable polymer and/or by the hydrophilicity or lipophilicity of the organic solvent that is used. The composition of the liquid polymer (i.e., the type of monomer used or the ratio of monomers for copolymers or terpolymers, the end groups on the polymer chains, and the molecular weight of the polymer) will determine the hydrophilicity or lipophilicity of the liquid polymer material as well as the degradation time of the liquid polymer implant. More hydrophilic liquid polymers (e.g., polylactic acid) and/or more hydrophilic solvents (e.g., N-methyl-2-pyrrolidone) can be used for active agents in applications where faster release rates and shorter durations of release (e.g., about 1-3 days) are needed. For slower releasing active agents and where longer durations of release for prolonged delivery (e.g., about 7-90 days) are desired, more hydrophobic and slower degrading liquid polymers (e.g., polycaprolactone) and/or more lipophilic solvents (e.g., triacetin) can be used to advantage. For even slower rates and longer durations of release of an active agent, the active agent itself can be made more water-insoluble by utilizing active agents, for example, in the form of lipophilic salts, drug complexes, and/or prodrug esters, amides or ethers. Thus, various forms of the drug or other biologically active agent can be used as needed. The composition includes the active agent in an amount effective to provide the desired therapeutic effect over the release period. The concentration range of the active agent in the composition will vary, for example, according to the active agent, the formulation and the rate of release from the implanted material, and can range, for example, from about 0.1% to about 30% by weight. The liquid polymer implant releases an effective amount of the bioactive agent by diffusion or dissolution from the liquid implant as it biodegrades in the body.

The terms biologically active agent, bioactive agent or active agent as used herein, refer to a drug or other substance that provides a biological effect and acts locally or systemically in the treatment, therapy, cure and/or prevention of a disease, disorder or other ailment. Representative biologically active agents include, without limitation, antibiotics, antimicrobials, anti-infectives, antigens, anti-allergenics, steroidal anti-inflammatory agents, non-steroidal anti-inflammatory agents, anti-tumor agents, anticancer drugs, decongestants, miotics, anti-cholinergics, sympathomimetics, sedatives, hypnotics, psychic energizers, tranquilizers, androgenic steroids, estrogens, progestational agents, LHRH agonists and antagonists, somatotropins, narcotic antagonists, humoral agents, prostaglandins, analgesics, antispasmodics, antimalarials, antihistamines, cardioactive agents, antiparkinsonian agents, antihypertensive agents, vaccines, antigens, anti-virals, antipsychotics, immunosuppressants, anesthetics, antifungals, antiproliferatives, anticoagulants, antipyretics, antispasmodics, growth factors, cell adhesion factors, cytokines, biological response modifiers, and nutritional agents. Examples of biologically-active agents include cisplatin, carboplatin, anastozole, fulvestrant, exemestane, estradiol, testosterone, misoprostol, follicle-stimulating hormone, dustasteride, doxycycline, ciprofloxacin, quinolone, ivermectin, haloperidol, diazepam, risperidone, olanzapine, naltrexone, fentanyl, buprenorphine, butorphanol, loperamide, nafarelin, buserelin, histrelin, deslorelin, leuprolide, goserelin, triptorelin, ganirelix, abarelix, cetrorelix, teverelix, octreotide, lanreotide, human growth hormone, interferon-alpha, interferon-beta, interferon-gamma, interleukin, calcitonin, growth hormone releasing peptides, glucagon-like peptides, granulocyte-colony stimulating factor, nerve growth factor, platelet-derived growth factor, insulin-like growth factor, vascular endothelial growth factor, fibroblast growth factor, bone morphogenic protein, erythropoietin, and salts, complexes, prodrugs, and analogs thereof.

The biologically active agent can be, for example, a simple organic compound, peptide, protein, DNA, or RNA material. The biologically active agent can be in the form of a liquid or a finely divided solid that is either dissolved or dispersed in the liquid polymer/solvent composition. The active agent is incorporated into the composition in an amount sufficient to achieve the desired therapeutic effect, the desired release profile, and the desired period of release of the active agent. There is no critical upper limit on the amount of the active agent that is dispersed or dissolved in the liquid polymer/solvent solution as long as the solution has a fluid viscosity acceptable for injection through a small gauge syringe needle (e.g., gauge of 18-26). The lower limit of the biologically active agent incorporated into the liquid polymer/solvent solution is dependent upon the activity of the active agent, the release rate needed to achieve the desired therapeutic level, and the length of time for treatment. The biologically active agent is typically present in the composition at a range from about 0.1 percent to about 30 percent by weight relative to the total weight of the composition, and more preferably, at a range from about 1 percent to 15 percent by weight. Both soluble and insoluble biologically active agents can be incorporated into the liquid polymer/solvent system. Embodiments of the liquid polymer/solvent/drug compositions include formulations with lactide/caprolactone liquid polymers dissolved in N-methyl-2-pyrrolidone at about 40% to about 70% by weight liquid polymer and containing, for example, cisplatin at about 4-12% or preferably about 8% by weight, carboplatin at about 5-15% or preferably about 10% by weight, buprenorphine at about 0.1-4% or preferably about 1.0% by weight, doxycyline hyclate at about 6-14% or preferably about 10% by weight, haloperidol at about 1-4% or preferably about 2% by weight, and triptorelin pamoate at about 2-10% or preferably about 5% by weight, the % by weight relative to the total weight of the composition.

The compositions can optionally include one or more adjuvants or additives, for example, biocompatible and nontoxic colorants, diluents, odorants, carriers, excipients, stabilizers, release rate modifiers, or the like.

The components for forming the compositions of the invention can be separate packaged and combined within a packaging as a kit. For example, an embodiment of a kit can include a container of a pharmaceutically-acceptable biodegradable liquid polymer, copolymer or terpolymer, a container of a biocompatible organic solvent that is dissolvable or dispersible in situ in a body fluid, and optionally at least one of a container of a therapeutically effective amount of a biologically active agent in a pharmaceutically-acceptable carrier or diluent, a syringe or other device for administering the liquid composition, and instructions or directions for preparation and administration of the compositions to form a polymeric implant. Alternatively, an embodiment of a kit can contain a syringe of the liquid polymer/solvent composition and a separate syringe with the biologically active agent which can be coupled together for mixing the biologically agent within the liquid polymer/solvent composition prior to injection in the body. Another embodiment of a kit can include a container or syringe of the liquid polymer/solvent/biologically active agent if the agent is stable in the liquid polymer solution.

EXAMPLES

The following examples are set forth as representative of the present invention. These examples are not to be construed as limiting the scope of the invention as these and other equivalent embodiments will be apparent in view of the present disclosure and accompanying claims.

Example 1

Preparation of a 50/60 DL-Lactide/Caprolactone Liquid Polymer with Higher Molecular Weight and Higher Fluid Viscosity (50/50 DL-PLC-HMW)

A 250 mL, round-bottom single neck flask was dried with a blow dryer and flushed with nitrogen for several minutes. Then a glass T-joint was placed in the top of the flask, a nitrogen inlet was connected to the side of the T-joint, and the top of the T-joint was connected to rubber tubing which led to a glass pipette immersed in water. The nitrogen flow was set so as to provide a steady bubbling of nitrogen in the water.

The catalyst system was prepared by dissolving 0.2710 grams of Tin(II) 2-ethylhexanoate in 2 mL of toluene in a small vial. The vial was flushed with nitrogen and capped.

Next, 72.3 grams (0.50 moles) of DL-lactide (Purac) was weighed and placed into the round-bottom flask. Then 57.1 grams (0.50 moles) of $\epsilon$-caprolactone (Fluka) was weighed and placed in the flask. To this mixture was added 5.6 mL (0.025 moles) of dodecanol and 0.1 mL of the Tin catalyst. The round-bottom flask was placed in an oil bath and heated at 160° C. for 18 hours with stirring by a magnetic stirring bar. The flask was cooled to 110° C. and a vacuum was pulled for 12 hours to remove any residual monomer. The flask was then cooled to room temperature, the vacuum released, and the thick viscous liquid polymer transferred to a sealed glass container. A total of 96.7 grams of the viscous liquid polymer was obtained. The molecular weight ($M_W$) of the copolymer as determined by gel permeation chromatography with a multi-angle light-scattering detector (GPC-MALS) was 8250 daltons with a polydispersity ($M_W/M_N$) of 1.13.

Example 2

Preparation of a 50/50 DL-Lactide/Caprolactone Liquid Polymer with Lower Molecular Weight and Lower Fluid Viscosity (50/50 DL-PLC-LMW)

The procedure in Example 1 was substantially repeated except that 13.6 mL (0.061 moles) of dodecanol and 0.1 mL of Tin catalyst were added to 72.1 grams (0.50 moles) of DL-lactide and 57.2 grams (0.50 moles) of caprolactone. The mixture was heated at 160° C. for 20 hours and the residual monomer removed under vacuum at 110° C. for 12 hours. A total of 123.1 grams of the viscous liquid polymer was obtained after transfer to a sealed glass container. The fluid viscosity of this copolymer was lower than that of the copolymer obtained in Example 1 as evidenced by the amount of polymer that could be poured from the round-bottom flask into the sealed glass container. The color of this copolymer was also a little more yellow than that of the copolymer prepared in Example 1. The molecular weight (Mw) of this liquid polymer as determined by GPC-MALS was 5903 daltons and the polydispersity ($M_W/M_N$) was 1.3.

Example 3

Preparation of an 80/20 Solution of the Higher Viscosity Liquid Polymer in N-Methyl-2-Pyrrolidone The higher molecular weight and higher fluid viscosity copolymer obtained in Example 1 (23.1 grams) was weighed into a glass contained and 5.8 grams of N-methyl-2-pyrrolidone (NMP) was added to the liquid polymer. The mixture was heated with a blow dryer in efforts to completely dissolve the copolymer; however, the complete dissolution required stirring the contents with a spatula for about 15 minutes to obtain a solution with 80% w/w copolymer and 20% w/w NMP. The solution was still viscous, but more flowable than the liquid polymer without solvent.

Example 4

Preparation of a 60/40 Solution of the Higher Viscosity Liquid Polymer in N-Methyl-2-Pyrrolidone 14.6 grams of the higher molecular and higher fluid viscosity liquid copolymer obtained in Example 1 was weighed into a glass container and 9.6 grams of NMP were added to the liquid polymer. The mixture was then stirred with a spatula for several minutes to fully dissolve the polymer. The resultant liquid polymer solution with 60% w/w copolymer and 40% NMP was much less viscous than the solution obtained in Example 3.

Example 5

Preparation of an 80/20 Solution of the Lower Viscosity Liquid Polymer in N-Methyl-2-Pyrrolidone The lower molecular weight and lower fluid viscosity copolymer obtained in Example 2 (23.1 grams) was weighed into a glass container and 5.8 grams of NMP were added to the liquid copolymer. The mixture was then stirred with a spatula until the polymer was completely dissolved. The resultant liquid polymer solution with 80% w/w liquid copolymer and 20% w/w NMP had about the same flow viscosity as the 60/40 solution of the higher molecular weight copolymer described in Example 4.

Example 6

Preparation of a Cisplatin/Liquid Polymer Formulation

The lower molecular weight copolymer obtained in Example 2 (29.2 grams) was weighed into a glass container and 19.5 grams of NMP were added to the copolymer. The mixture was then stirred vigorously with a spatula until all of the copolymer had dissolved to give a solution with 60% w/w copolymer and 40% w/w NMP. This liquid polymer solution was drawn up into a large plastic syringe and the desired amount of polymer solution was transferred to 1.2 mL male luer-lok gamma resistant polypropylene syringes using a stainless steel female coupler. After the filling operation, each syringe was capped with a female luer-lok polypropylene cap, and the syringes were placed in a bag for sterilization by exposure to gamma irradiation at 25 kGy.

Cisplatin powder was then weighed out in plastic trays at the amounts required to give formulations with 8% by weight drug when mixed with the liquid polymer solutions, and the drug was transferred to female luer-lok polypropylene syringes with the plungers removed. After placing the cisplatin in the syringes from the top of the syringe with the caps in place, the plungers were re-inserted into the syringes, the syringes were held with the tips up, the caps were loosened, and the plunger tips with the cisplatin contents were moved up toward the tips until there was only a slight space between the drug and the tip of the syringe. The caps were then tightened, and the syringes were set aside for labeling. The doses and fill weights that were prepared are listed in Table 1.

TABLE 1

Doses and Fill Weights of Cisplatin/Liquid Polymer Formulations

| Cisplatin Dose | Fill Weights of Syringes |
|---|---|
| 50 mg dose | 760 mg liquid polymer solution<br>66 mg cisplatin |
| 30 mg dose | 529 mg liquid polymer solution<br>46 mg cisplatin |
| 20 mg dose | 414 mg liquid polymer solution<br>36 mg cisplatin |
| 10 mg dose | 299 mg liquid polymer solution<br>26 mg cisplatin |

Example 7

Evaluation of the Cisplatin/Liquid Polymer Formulations in Dogs

The cisplatin/liquid polymer formulations described in Example 6 were evaluated in dogs with various forms of cancer. The specific dose of cisplatin administered in the liquid polymer formulation was determined by the weight of the dog being treated.

Prior to administration, a syringe filled with the liquid polymer solution was coupled to the cisplatin dry powder syringe using the luer-lok system. The contents of the liquid polymer solution were then passed into the cisplatin powder syringe by pressing on the plunger. The mixture of cisplatin powder and liquid polymer solution was then moved back into the liquid polymer syringe, and this step was completed for about 50 back and forth times to complete the mixing of the cisplatin with the liquid polymer solution. The homogenous mixture was then pulled back into the liquid polymer syringe, the two syringes decoupled, and a syringe needle attached to the liquid polymer syringe with the cisplatin/liquid polymer formulation. The formulation was next injected intramuscularly into the animal at the desired dosage using a 20 gauge needle. Samples of blood from the treated animals were taken at baseline and after 1, 2, 3, and 4 weeks and analyzed for neutrophil levels as an indication of the release and activity of the cisplatin. Cisplatin is an anti-cancer drug known to reduce neutrophil counts in dogs when administered intravenously as an aqueous solution.

With each animal, the neutrophil counts started to drop immediately after administration of the formulation indicating that active cisplatin was being released. The neutrophil counts continued to decrease with minimum values being reached at about two weeks, after which the values slowly increased. These data showed that the cisplatin was being released from the liquid polymer formulation in a sustained release manner. A comparison of the neutrophil levels obtained with the liquid polymer formulation to that obtained with a similar formulation using a solid 50:50 poly(DL-lactide-co-glycolide) (PLG) polymer dissolved in NMP is given in Table 2.

TABLE 2

Comparison of Neutrophil Counts with Cisplatin Formulations

| Polymer | Neutrophil Count | | | | |
| --- | --- | --- | --- | --- | --- |
|  | Initial | Week 1 | Week 2 | Week 3 | Week 4 |
| Solid PLG | 12.32 | 8.46 | 7.11 | 7.36 | 12.36 |
| Liquid PLC | 11.16 | 6.72 | 5.30 | 9.02 | 12.08 |

These data show that the liquid polymer formulation resulted in lower levels of neutrophils than the solid polymer formulation, indicating a more active release of cisplatin, and surprisingly, the reduction in neutrophils levels were sustained for about the same length of time with the two formulations.

Example 8

Preparation of a Buprenorphine HCL/Liquid Polymer Formulation 6.0 grams of the lower molecular weight copolymer described in Example 2 was dissolved in 6.0 grams of NMP to give a solution with 50% w/w copolymer and 50% w/w NMP. This solution was non-viscous and could be easily pulled up into a syringe using a 20 gauge needle. 5.0 grams of this liquid polymer solution was placed in a glass ampule and 50 milligrams of buprenorphine HCL powder from a weigh cup was placed in the ampule with the polymer solution to provide a formulation with approximately 1% w/w drug. Buprenorphine is an opioid agonist-antagonist analgesic. The mixture was stirred vigorously with a spatula until it appeared that the buprenorphine HCL powder had fully dissolved. The polymer solution with the dissolved drug was then drawn up into a plastic syringe with a male luer-lok tip. The plastic syringe with the polymer/drug solution was attached to the female luer-lok tip of a sterile filter from Advantec Mfgs., Inc. The filter casing was polypropylene and the filter itself was hydrophobic Teflon with a pore size of 0.20 µm and a diameter of 25 mm. The liquid polymer/drug solution was easily forced through the 0.25 µm filter to provide a clear and sterile liquid polymer/solvent/buprenorphine HCL formulation which was placed in an ampule with a rubber cap and stored. Analysis of the formulation by ultraviolet (UV) visible spectroscopy showed that the drug was present at a concentration of 0.98% w/w.

Example 9

Evaluation of the Efficacy of a Buprenorphine HCL/Liquid Polymer Formulation in a Rat Pain Model Male Sprague Dawley rats were selected for the study involving the hot water tail flick procedure to determine the efficacy of the buprenorphine/liquid polymer formulation in reducing pain. Prior to administration of the formulations, each rat had its tail placed in a heated water bath to observe whether the animal felt the momentary discomfort from the heat and moved its tail in response to the heat stimulus. The length of time in seconds required for the rat to move its tail was recorded. If the animal did not move its tail within 10 seconds, the tail was removed from the water bath.

Three rats were used for each test group. The three groups consisted of the liquid polymer/NMP solution without drug (vehicle control), the liquid polymer/NMP/buprenorphine HCL formulation at 0.6 mg dose of drug, and the liquid polymer/NMP/buprenorphine HCL formulation at 1.8 mg dose of drug. Each of the vehicle control animals was injected in the scapular region with 180 µl of the liquid polymer/NMP solution using a 20 gauge needle. The rats with a dose of 0.6 mg of drug were injected with 60 µL of the liquid polymer/drug solution, and the animals with a dose of 1.8 mg of drug were injected with 180 µL of the polymer/drug solution. All of the injections went well with no administration problems, no apparent implant bumps, and no apparent local tissue irritation effects. Each animal was then tested for its response to the hot water stimulus at 4, 8, 24, 32, 40, 52, 60, and 72 hours. The results are given Table 3.

TABLE 3

Hot Water Tail Flick Results with Liquid Polymer/Buprenorphine Formulation

| | Response Time (seconds) | | |
| --- | --- | --- | --- |
| Time point | Vehicle | 0.6 mg Dose | 1.8 mg Dose |
| Initial | 1.00 | 1.00 | 1.66 |
| 4 hours | 2.00 | 5.66 | 5.00 |
| 8 hours | 2.00 | 6.00 | 4.66 |
| 24 hours | 2.00 | 3.66 | 3.33 |
| 32 hours | 1.33 | 3.00 | 3.33 |
| 40 hours | 2.00 | 2.33 | 4.33 |
| 52 hours | 1.33 | 2.00 | 3.33 |
| 60 hours | 1.66 | 2.66 | 2.66 |
| 72 hours | 1.33 | 2.00 | 2.33 |

The data show that at all time points the response times were longer with the buprenorphine liquid polymer formulations than with the vehicle control. This indicates that the drug was being released in an active form up to 72 hours. Normally, buprenorphine HCL given in an aqueous solution provides efficacy in the rat tail flick test for only about 5 hours, therefore, extended release of the active drug was provided by the liquid polymer formulation.

Example 10

Preparation of a Buprenorphine Base/Liquid Polymer Formulation 10 grams of the lower molecular weight copolymer described in Example 2 was dissolved in 10.1 grams of NMP to give a solution with 50% w/w copolymer and 50% w/w NMP. To this solution was added 0.2085 grams of buprenorphine base. The white powdered base was thoroughly mixed and particles crushed until a clear solution was obtained. Then 0.4170 grams of palmitic acid was added to the polymer/drug/NMP solution to complex with the buprenorphine base to form buprenorphine palmitate. The white flaky palmitic acid was crushed and thoroughly mixed until a clear solution was obtained. The resultant solution was then filtered through a 0.20 µm Teflon filter as described in Example 8 to produce a sterile solution with 1% w/w buprenorphine and 2% w/w palmitic acid. The sterile solution was stored in a glass ampule with a rubber cap until needed.

Example 11

Pharmacokinetic Evaluation of Buprenorphine/Liquid Polymer Formulations

Samples of the buprenorphine HCL/liquid polymer formulation described in Example 8 and the buprenorphine base/liquid polymer formulation described in Example 10 were evaluated in dogs for in vivo release of the drug. A commercially available aqueous solution of buprenorphine HCL (Buprenex®) was used as the control. The Buprenex® control formulation was administered to the dogs subcutaneously every 8 hours at a dose of 0.03 mg/kg for 64 hours (nine administrations) to give a total dose of 0.27 mg/kg. The two liquid polymer formulations were administered only once at a total dose of 0.27 mg/kg to match the dose given with the Buprenex® control. Samples of blood were collected from the dogs at 0 (pre-dose administration), and 1, 4, 8, 12, 24, 48, 72, and 90 hours post-administration and separated into plasma for analysis of buprenorphine concentration by liquid chromatography/mass spectroscopy (LC/MS/MS). A total of three dogs were used with each dog receiving one of the three test articles at the initiation of the study and a different test article 10 days later until each dog had received all three formulations. The results are presented in Table 4.

TABLE 4

Pharmacokinetics of Buprenorphine/Liquid Polymer Formulations

| | Buprenorphine Plasma Concentration, ng/mL | | |
|---|---|---|---|
| Time, hrs | Buprenex ® | Polymer/HCL | Polymer/Base |
| 0 | 0 | 0 | 0 |
| 1 | 5.46 | 2.14 | 0 |
| 4 | 1.86 | 1.88 | 0.25 |
| 8 | 0.99 | 1.57 | 0.83 |
| 12 | 2.84 | 1.58 | 0.97 |
| 24 | 1.72 | 1.69 | 1.26 |
| 48 | 2.30 | 1.30 | 1.38 |
| 72 | 2.24 | 1.21 | 1.24 |
| 90 | 0.57 | 0.57 | 0.63 |

The data show that the liquid polymer formulations gave lower initial plasma levels of drug in the dogs than the Buprenex® control formulation even though nine times the amount of buprenorphine were administered initially as the control. These data indicate that the liquid polymer delivery system was able to suppress the initial burst of drug to safe levels. The data also show that the liquid polymer/base formulation with the addition of palmitic acid to form the palmitate salt completely suppressed the initial burst of drug with a resultant delay in drug release. The almost constant levels of buprenorphine obtained with the liquid polymer formulations over the 72 hours of the study are a good indication of the controlled release of the drug from the liquid polymer delivery system. In contrast, the plasma levels with the Buprenex® control formulation were more erratic due to the administration every 8 hours. Based upon the plasma levels obtained with the liquid polymer formulations, it appears that they will provide with only one administration the same degree of pain control as the Buprenex® control with eight administrations, and they will do this without any burst effects from the polymer system.

Example 12

Evaluation of Doxycycline Hyclate/Liquid Polymer Formulations for In Vitro Release of Drug The 60/40 liquid polymer solution described in Example 4 was used to fill a 1.2 cc polypropylene syringe with male luer-lok fittings to about 0.5 cc of polymer solution. Also, a small amount of the nonpolymeric material, palmitic acid, was added to a container with some of the 60/40 liquid polymer solution to give a solution containing by weight 54% liquid polymer, 36% NMP, and 10% palmitic acid. About 0.5 cc of this solution was filled into a 1.2 cc polypropylene syringe with a male luer-lok fitting. Next, a small amount of the higher viscosity liquid polymer described in Example 1 was dissolved in triacetin, a more lipophilic solvent, at 50% w/w polymer and 50% w/w triacetin. About 0.5 cc of this liquid polymer solution was also filled into a polypropylene syringe. Each of the syringes with the liquid polymer solutions were connected to a female luer-lok polypropylene syringe containing 50 mg of doxycycline hyclate powder, and the contents of the syringe moved back and forth between the two syringes 50 times. Doxycycline is a broad-spectrum tetracycline antibiotic. Similarly, a control sample of the solid polymer, poly(DL-lactide) dissolved in NMP at a ratio of 37% w/w polymer to 63% w/w NMP was also mixed with 50 mg of doxycycline hyclate for 50 times. The thoroughly mixed formulations were then drawn back into the male syringe, the two syringes decoupled, and the contents of the syringes injected without a needle into small containers with 10 mL of water.

Each of the formulations before injection into the water was yellow due to the color of the doxycycline, and the release of the drug could be easily followed by observing the color of the water receiving fluid. The solid polymer/doxycycline formulation gave a solid intact mass immediately upon insertion into the water receiving fluid. All of the liquid polymer/doxycycline formulations gave liquid films upon insertion into the water receiving fluids. Both the 60/40 liquid polymer/NMP and the 54/36/10 liquid polymer/NMP/palmitic acid formulations gave liquid films upon the top of the water whereas the liquid polymer/triacetin formulation formed a liquid film at the bottom of the water container. With time, the liquid polymer/palmitic acid formulation tended to thicken whereas the other liquid polymer formulations remained fluid liquids.

Surprising, after ten hours, it was apparent from the color of the receiving fluids that the solid polymer formulation had released more drug than the other formulations. The amount of drug release was in the order of the solid polymer/NMP>50/50 liquid polymer/triacetin>60/40 liquid polymer/NMP>54/36/10 liquid polymer/NMP/palmitic acid. After 20 hours, the order of drug release was solid polymer/NMP>50/50 liquid polymer/triacetin>54/36/10 liquid polymer/NMP/palmitic acid>60/40 liquid polymer/NMP. After three days, the 60/40 liquid polymer/NMP and the 54/36/10 liquid polymer/NMP/palmitic acid still had some yellow color in the liquid implant whereas the solid polymer/NMP implant was white. These data showed that surprisingly the liquid polymer formulations gave less of a drug burst and more sustained release than the solid polymer formulation.

Example 13

Preparation and Evaluation of a Haloperidol/Liquid Polymer Formulation 24.5 grams of the 50/50 DL-PLC lower viscosity liquid polymer prepared as described in Example 2 was dissolved in 24.5 grams of NMP to give 49.0 grams of a 50/50 liquid polymer/NMP solution. To this solution was added 1.004 grams of haloperidol base and the mixture was stirred vigorously with slight heating until all of the drug had completely dissolved to give a clear solution with 2% by weight haloperidol. The drug/polymer solution was then filtered through a 0.20 μm Teflon filter as described in Example 8. The haloperidol/liquid polymer formulation was then tested for efficacy in both bighorn sheep and elk by observation of the extent and duration of sedation in the animals. Three bighorn sheep were each injected with 2.0 mL of the formulation and three elk were each injected with 3.0 mL of the formulation. In each animal, mild sedation was observed for 72 hours. Both the extent and duration of sedation was sufficient for handling and moving the animals without harm.

Example 14

Preparation of a 25/75 DL-Lactide/Caprolactone Liquid Polymer with a Higher Molecular Weight and Higher Fluid Viscosity 25/75 DL-PLC-HMW)

The procedure as described in Example 1 was substantially repeated except that the reaction flask was filled with 36.0 grams (0.25 moles) of DL-lactide and 85.7 grams (0.75 moles) of caprolactone. To this mixture was added 5.6 mL (0.025 moles) of dodecanol and 0.10 mL of the Tin catalyst. The mixture was heated at 160° C. for 18 hours and the residual monomer removed under vacuum at 110° C. for 8 hours. A total of 108.5 grams of a viscous polymer was obtained. The liquid polymer material had a slightly yellow color and a sweet smell. The polymer appeared to be somewhat less viscous than the 50/50 PLC liquid polymer material prepared in Example 1 even though the molecular weight as determined by GPC-MALS was higher at 9909 daltons with a polydispersity of 1.18.

Example 15

Preparation of a 75/25 DL-Lactide/Caprolactone Liquid Polymer with a Higher Molecular Weight and Higher Fluid Viscosity (75/25 DL-PLC-HMW)

The procedure as described in Example 14 was substantially repeated except that the reaction flask was charged with 108.1 grams (0.75 moles) of DL-lactide and 28.5 grams (0.25 moles) of caprolactone. The same amount of dodecanol (5.6 mL, 0.025 moles) and Tin catalyst (0.10 mL) were used as were the reaction temperatures and times. A total of 85.3 grams of a thick viscous polymer were obtained with considerable polymer left in the reaction flask. This polymer was the most viscous of all the polymers prepared but still flowed as a liquid. The liquid polymer had a molecular weight as determined by GPC-MALS of 8086 daltons with a polydispersity of 1.21.

Example 16

Preparation of a 75/25 DL-Lactide/Caprolactone Liquid Polymer with a Lower Molecular Weight and Lower Fluid Viscosity (75/25 DL-PLC-LMW)

The procedure as described in Example 15 was substantially repeated except that 13.6 mL (0.061 moles) of dodecanol was used as the initiator or chain terminator. The reaction mixture was heated at 160° C. for 20 hours and the residual monomer removed at 110° C. for 12 hours. A total of 109.5 grams of polymer was obtained with some residual polymer left in the reaction flask. This liquid polymer with a molecular weight of 4159 daltons and a polydispersity of 1.67 was less viscous than the 75/25 PLC polymer prepared in Example 15.

Example 17

Preparation of Triptorelin Pamoate/Liquid Polymer Formulations

A number of different liquid polymers and biocompatible solvents were combined to produce the following test solutions:

Solution A: 2.5 grams of the 50/50 DL-PLC-HMW polymer described in Example 1 was dissolved in 1.7 grams of NMP to give a formulation with a 60/40 polymer/NMP weight ratio.

Solution B: 2.6 grams of the 50/50 DL-PLC-HMW polymer described in Example 1 was dissolved in 2.6 grams of methoxypolyethylene glycol (MPEG) to give a formulation with 50/50 polymer/MPEG weight ratio.

Solution C, 2.7 grams of the 50/50 DL-PLC-HMW polymer described in Example 1 was dissolved in 2.9 grams of triacetin to give a formulation with a 48/52 polymer/triacetin ratio.

Solution D: 2.7 grams of the 25/75 DL-PLC-HMW polymer described in Example 14 was dissolved in 1.9 grams of NMP to give a formulation with a 59/41 polymer/NMP weight ratio.

Solution E: 2.3 grams of the 75/25 DL-PLC-LMW polymer described in Example 16 was dissolved in 1.6 grams of NMP to give a formulation with a 59/41 polymer/NMP weight ratio.

The flow viscosity of each of the solutions was dependent upon the specific solvent used, the polymer composition, and its molecular weight. Solutions B and C with the poorer solvents were more viscous than Solutions A and D. As expected Solution E with the lower molecular weight polymer in the better solvent, NMP, gave the lowest flow viscosity. However, all solutions of the liquid polymers could be easily expressed through a 22 gauge needle using a 500 μL Hamilton syringe.

Approximately 1.0 grams of each polymer solution was weighed into a 10-mL glass scintillation vial, and about 50 mg of triptorelin pamoate weighed out in a weigh boat was added to the polymer solution to provide test formulations with 5% by weight of triptorelin pamoate. The dispersion of the powdered drug in the polymer solutions was highly dependent upon the solvent in the formulation. In all of the formulations with NMP as the solvent, the triptorelin pamoate immediately formed a gummy ball around the spatula used for mixing. Vigorous stirring and breaking up of the gum ball was required to obtain a fine dispersion of the drug within the formulation. With the formulation containing methoxypolyethylene glycol, the triptorelin pamoate appeared to disperse well with stirring initially. However, upon standing overnight, the drug appeared to ball up just like that observed with the NMP formulations. Once again, vigorous stirring and crushing of the gum ball was required to obtain a fine dispersion of the drug in the liquid polymer/solvent formulation. The formulation containing triacetin as the solvent behaved the best upon addition of the triptorelin pamoate. The drug dispersed well to form a liquid formulation in the form of a fine creamy dispersion which was maintained over time.

Example 18

Evaluation of the Triptorelin Pamoate/Liquid Polymer Formulations for Efficacy in Rats Approximately 300-400 μL of each test formulation was loaded into a 500 μL Hamilton syringe and injected through a 22 gauge needle at a dose of 50 μL into male Sprague Dawley rats weighing approximately 250 grams. Five rats were used for each test formulation. Samples of blood were drawn from each rat immediately prior to test article administration and again on Days 14, 28, 56, 84, and 105. The blood samples were separated into serum (about 0.35 mL) and frozen at −80° C. until the end of the study. The serum samples were then assayed for testosterone concentration using an RIA method. The results of the assays are given in Table 5.

TABLE 5

Efficacy of Triptorelin Pamoate/Liquid Polymer Formulations

| | Serum Testosterone Concentration, ng/mL | | | | |
|---|---|---|---|---|---|
| Formulation | Day 0 | Day 14 | Day 28 | Day 56 | Day 84 | Day 105 |
| A | 1.86 | 1.00 | 0.96 | 1.39 | 1.14 | 0.52 |
| B | 1.64 | 1.36 | 1.66 | 1.88 | 1.11 | 1.89 |
| C | 1.28 | 0.65 | 0.50 | 0.74 | 0.91 | 1.32 |
| D | 1.31 | 0.91 | 0.60 | 0.53 | 0.79 | 1.31 |
| E | 1.67 | 1.69 | 1.08 | 1.51 | 1.88 | 1.58 |

The reduction in testosterone levels from the baseline value can be used to compare the long-term release of the triptorelin pamoate LHRH agonist. If the drug is being released in a bioactive form and at a sufficient rate, then the testosterone levels should decrease to approximately the same level as castrated rats. As shown by the data in Table 5, Formulations B and E did not provide effective reductions in testosterone levels. Formulation A did lower the testosterone levels from baseline values, but the reductions were not effective until the last time point. Formulations C and D effectively reduced testosterone levels to essentially castrate levels with the reductions in testosterone being maintained for at least 84 days. Surprisingly, these reductions in testosterone levels compare favorably with those reported in the literature for three-month extended released leuprolide LHRH formulations using a solid polymer implant or microspheres.

The results indicate that the solvent affects the release of the triptorelin pamoate as Sample C, which gave effective reductions of testosterone over the desired time period, contained the lipophilic solvent, triacetin. Samples A and B with the same liquid polymer but dissolved in the hydrophilic solvents, NMP and MPEG, did not give the desired release of drug and testosterone suppression. Although Sample D was also formulated with the hydrophilic NMP solvent, the 25/75 lactide/caprolactone liquid polymer used in this formulation was more hydrophobic than the 50/50 lactide/caprolactone liquid polymer used in Sample A as it had a higher molar ratio of caprolactone. These results indicate that for the lipophilic drug, triptorelin pamoate, the more lipophilic liquid polymer formulations provided the desired release profile and testosterone suppression.

Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations that operate according to the principles of the invention as described. Therefore, it is intended that this invention be limited only by the claims and the equivalents thereof. The disclosures of patents, references and publications cited in the application are incorporated by reference herein.

What is claimed is:

1. A liquid polymer composition formulated for administering into a body of an animal or human, comprising:
   (a) a biodegradable liquid polymer comprising a copolymer of lactide and caprolactone with a molar ratio from 75/25 to 25/75 and a molecular weight of 2000 daltons to 20,000 daltons, the molecular weight as determined by gel permeation chromatography using a multi-angle light-scattering detector (GPC-MALS);
   (b) a biocompatible organic solvent; and
   (c) a therapeutically effective amount of a biologically active agent;
   wherein the composition, when placed in contact with body fluid of an animal or human, remains in a liquid form and does not form a solid in situ after dissipation of the organic solvent from the composition into said body fluid.

2. The composition of claim 1, wherein the solvent comprises a hydrophilic organic solvent having a water solubility greater than 10% by weight of said solvent in water.

3. The composition of claim 1, wherein the solvent comprises a hydrophilic organic solvent selected from the group consisting of N-methyl-2-pyrrolidone, 2-pyrrolidone, N-ethyl-2-pyrrolidone, N-cyclohexyl-2-pyrrolidone, N-hydroxethyl-2-pyrrolidone, dimethyl acetamide, dimethyl formamide, acetic acid, lactic acid, ethanol, propanol, methyl lactate, ethyl lactate, methyl acetate, diethylene glycol monomethyl ether, glycofurol, glycerol formal, isopropylidene glycerol, dimethyl sulfoxide, ε-caprolactone, butyrolactone, propylene glycol, polyethylene glycol, glycerol, 1,3-butyleneglycol, methoxypolyethylene glycol, methoxypropylene glycol, acetone, methyl ethyl ketone, tetrahydrofuran, and combinations thereof.

4. The composition of claim 1, wherein the solvent comprises a hydrophilic organic solvent selected from the group consisting of N-methyl-2-pyrrolidone, 2-pyrrolidone, dimethyl acetamide, dimethyl sulfoxide, ethyl lactate, glycofurol, glycerol formal, isopropylidene glycerol, propylene glycol, polyethylene glycol, methoxypolyethylene glycol, methoxypropylene glycol, and combinations thereof.

5. The composition of claim 1, wherein the solvent comprises a lipophilic organic solvent having a water solubility less than 10% by weight of the solvent in water.

6. The composition of claim 1, wherein the solvent comprises a lipophilic organic solvent selected from the group consisting of ethyl acetate, ethyl butyrate, ethyl oleate, isopropyl palmitate, ethyl palmitate, methyl palmitate, isopropyl myristate, diethyl malonate, diethyl succinate, dimethyl adipate, dimethyl succinate, dibutyl sebacate, triacetin, triethyl citrate, tributyrin, acetyl triethyl citrate, acetyl tributyl citrate, acetyl trihexyl citrate, butyryl trihexyl citrate, tributyl citrate, caprylic/capric triglycerides, caprylic/capric/linoleic triglyceride, caprylic/capric/succinic triglyceride, propylene glycol dicaprylate/caprate, benzyl alcohol, ethyl benzoate, benzyl benzoate, propylene carbonate, dimethyl carbonate, N,N-diethyl-toluamide, N-dodecyl-2-pyrrolidone, N-octyl-2-pyrrolidone, N-methyl-2-caprolactam, N-dodecyl-caprolactam, heptanoic acid, oleic acid, sesame oil, peanut oil, castor oil, and combinations thereof.

7. The composition of claim 1, wherein the solvent comprises a lipophilic organic solvent selected from the group consisting of ethyl acetate, ethyl oleate, isopropyl myristate, triacetin, triethyl citrate, acetyl tributyl citrate, ethyl benzoate, benzyl benzoate, sesame oil, and combinations thereof.

8. The composition of claim 1, wherein the solvent comprises a combination of a hydrophilic solvent and a lipophilic solvent.

9. The composition of claim 1, wherein the biodegradable liquid polymer is pharmaceutically-acceptable.

10. The composition of claim 1, wherein the organic solvent is dissolvable or dispersible in situ in a body fluid of an animal or human.

11. The composition of claim 1, wherein the composition when placed in a body of an animal or human, forms a biodegradable polymeric implant having a liquid consistency.

12. The composition of claim 1, comprising 30-90% by weight liquid polymer and 10-70% by weight organic solvent, the % by weight based on the total weight of the composition.

13. The composition of claim 1, comprising 0.1-30% by weight active agent.

14. The composition of claim 1, wherein the biologically active agent is selected from the group consisting of cisplatin, carboplatin, anastozole, fulvestrant, exemestane, estradiol, testosterone, misoprostol, follicle-stimulating hormone, dustasteride, doxycycline, ciprofloxacin, quinolone, ivermectin, haloperidol, diazepam, risperidone, olanzapine, naltrexone, fentanyl, buprenorphine, butorphanol, loperamide, nafarelin, buserelin, histrelin, deslorelin, leuprolide, goserelin, triptorelin, ganirelix, abarelix, cetrorelix, teverelix, octreotide, lanreotide, human growth hormone, interferon-alpha, interferon-beta, interferon-gamma, interleukin, calcitonin, growth hormone releasing peptides, glucagon-like peptides, granulocyte-colony stimulating factor, nerve growth factor, platelet-derived growth factor, insulin-like growth factor, vascular endothelial growth factor, fibroblast growth factor, bone morphogenic protein, erythropoietin, and salts, complexes and prodrugs.

15. The composition of claim 1, wherein the organic solvent comprises N-methyl-2-pyrrolidone, and the biologically active agent is selected from the group consisting of cisplatin, carboplatin, buprenorphine, doxycycline, haloperidol, and triptorelin pamoate.

16. The composition of claim 1, wherein the organic solvent comprises triacetin, and the biologically active agent comprises triptorelin pamoate.

17. The composition of claim 1, wherein the copolymer of lactide and caprolactone has a molecular weight of 3,000 daltons to 12,000 daltons.

18. The composition of any of claims 1-17, wherein the biodegradable liquid polymer is a liquid at 25° C. up to 37° C.

19. The composition of any of claims 1-18, packaged for use in forming a biodegradable polymeric material or implant within a body of an animal or human.

20. The composition of any of claims 1-18, for use as a biodegradable polymeric implant to deliver the biologically active agent into a body of an animal or human.

21. Use of the composition of any of claims 1-18, in the preparation of a medicament for forming a biodegradable polymeric material or implant within a body of an animal or human to deliver the biologically active agent into the body.

22. A method of forming a biodegradable polymeric implant within a body of an animal or human, comprising:
administering into the body an amount of a liquid polymer composition comprising:
(a) a pharmaceutically acceptable, biodegradable liquid polymer comprising a copolymer of lactide and caprolactone with a molar ratio from 75/25 to 25/75 and a molecular weight of 2000 daltons to 20,000 daltons, the molecular weight as determined by gel permeation chromatography using a multi-angle light-scattering detector (GPC-MALS);
(b) a biocompatible organic solvent that is dissolvable or dispersible in situ in a body fluid of the animal or human; and
(c) a therapeutically effective amount of a biologically active agent; and
allowing the solvent to dissipate into body fluids within the body to form the biodegradable polymeric material having a liquid consistency which does not form into a solid in situ;
wherein the polymeric material releases the biologically active agent as the polymeric material biodegrades within the body.

23. The method of claim 22, wherein the liquid polymer composition is administered through a syringe or needle of 18-26 gauge.

24. The method of claim 22, wherein the liquid polymer composition is administered into a body tissue within the body of the animal or human to form a liquid implant.

25. The method of claim 22, wherein the implant is in the form of a film.

26. The method of claim 22, wherein the implant is in the form of a plug situated within the body tissue.

27. The method of claim 22, wherein the liquid polymer composition is administered onto a device selected from the group consisting of a catheter, a mesh, a screw, a plate, a tack, a pin, a staple, and a sponge, and the method further comprises placing the device with the composition thereon into the body of the animal or human.

28. The method of any of claims 22-27, further comprising, prior to administering the liquid polymer composition into the body of the animal or human, dissolving the biodegradable liquid polymer in the organic solvent, and adding an effective amount of the biologically active agent to the composition.

29. A kit comprising the composition of claim 1; and
directions for preparation and/or administration of the liquid polymer composition to form the polymeric implant.

30. A method of forming a biodegradable polymeric implant within a body of an animal or human, comprising:
administering into the body the liquid polymer composition of claim 1; and
allowing the solvent to dissipate into body fluids to form the biodegradable polymeric implant having a liquid consistency which does not form into a solid in situ, wherein the biologically active agent is released from the polymeric implant into the body over an extended time period as the polymeric implant biodegrades.

* * * * *

UNITED STATES PATENT AND TRADEMARK OFFICE
CERTIFICATE OF CORRECTION

PATENT NO. : 8,187,640 B2
APPLICATION NO. : 12/812670
DATED : May 29, 2012
INVENTOR(S) : Richard L. Dunn Page 1 of 1

It is certified that error appears in the above-identified patent and that said Letters Patent is hereby corrected as shown below:

On the Title page, insert item [63] as follows:

--Related U.S. Application Data

PCT/US2009/030853, filed on January 13, 2009, which is a continuation-in-part of application No. 12/100,562, filed on April 10, 2008, now abandoned, which is a continuation-in-part of application No. 12/013,912, filed on January 14, 2008, now abandoned.--

Signed and Sealed this
Twenty-eighth Day of August, 2012

David J. Kappos
*Director of the United States Patent and Trademark Office*